US012653784B2

(12) United States Patent  
Barenholz et al.

(10) Patent No.: US 12,653,784 B2  
(45) Date of Patent: Jun. 16, 2026

(54) DETERMINATION OF THE TRAPPED VOLUME OF A LIPOSOME

(71) Applicants: Moebius Medical Ltd., Tel Aviv (IL); Yissum Research Development Company of the Hebrew University of Jerusalem Ltd., Jerusalem (IL)

(72) Inventors: Yechezkel Barenholz, Jerusalem (IL); Keren Turjeman, Jerusalem (IL); Ron Pinkus, Raanana (IL)

(73) Assignees: Moebius Medical Ltd., Tel Aviv (IL); Yissum Research Development Company of the Hebrew University of Jerusalem Ltd., Jerusalem (IL)

( * ) Notice: Subject to any disclaimer, the term of this patent is extended or adjusted under 35 U.S.C. 154(b) by 177 days.

(21) Appl. No.: 18/725,983

(22) PCT Filed: Jan. 1, 2023

(86) PCT No.: PCT/IL2023/050003  
§ 371 (c)(1),  
(2) Date: Jul. 1, 2024

(87) PCT Pub. No.: WO2023/126947  
PCT Pub. Date: Jul. 6, 2023

(65) Prior Publication Data  
US 2025/0114303 A1 Apr. 10, 2025

Related U.S. Application Data

(60) Provisional application No. 63/295,896, filed on Jan. 2, 2022.

(51) Int. Cl.  
*A61K 9/127* (2025.01)  
*G01N 33/15* (2006.01)

(52) U.S. Cl.  
CPC ............. *A61K 9/127* (2013.01); *G01N 33/15* (2013.01)

(58) Field of Classification Search  
CPC ............................... A61K 9/127; G01N 33/15  
See application file for complete search history.

(56) References Cited

U.S. PATENT DOCUMENTS

| | | | |
|---|---|---|---|
| 5,192,549 A | 3/1993 | Barenholz et al. | |
| 6,086,851 A | 7/2000 | Boni | |
| 6,696,080 B1 | 2/2004 | Bolotin et al. | |
| 2020/0170948 A1 | 6/2020 | Barenholz et al. | |

OTHER PUBLICATIONS

Barenholz et al., (1993) "Quality Control Assays in the Development and Clinical Use of Liposome-Based Formulations," Liposome Technology, 2nd Edition, vol. 1, Liposome Preparation and Related Techniques, Edited by Gregory Gregoriadis, CRC Press, Boca Raton. pp. 527-616.

Cohen et al., (2012) "Prolonged analgesia from Bupisome and Bupigel formulations: From design and fabrication to improved stability," J Control Release 160(2): 346-352.

Elorza et al., (1993) "Comparison of particle size and encapsulation parameters of three liposomal preparations," J. Microencapsulation 10(2): 237-248.

MacDonald et al., (1993) "Applications of Freezing and Thawing in Liposome Technology," Liposome Technology, 2nd Edition, vol. 1, Edited by Gregory Gregoriadis, CRC Press, Boca Raton. pp. 209-228.

Mayer et al., (1985) "Solute distributions and trapping efficiencies observed in freeze-thawed multilamellar vesicles," Biochim Biophys Acta 817(1): 193-196.

Oku et al., (1982) "A Simple Procedure for the Determination of the Trapped Volume of Liposomes," Biochimica et Biophysica Acta (BBA)—Biomembranes 691(2): 332-340.

Perkins et al., (1993) "The determination of liposome captured volume," Chemistry and Physics of Lipids 64(1-3): 197-217.

Pick (1982) "Liposomes with a Large Trapping Capacity Prepared by Freezing and Thawing of Sonicated Phospholipid Mixtures," Arch Biochem Biophys 212(1): 186-194.

Samuni et al. (1997) "Stable Nitroxide Radicals Protect Lipid Acyl Chains from Radiation Damage," Free Radic Biol Med 22(7): 1165-1174.

Schafer et al., (1964) "Permeability of mammalian heart capillaries to sucrose and inulin," Am J Physiol 206: 985-991.

Shmeeda et al., (2003) "Enzymatic Assays for Quality Control and Pharmacokinetics of Liposome Formulations: Comparison with Nonenzymatic Conventional Methodologies," Methods Enzymol 367: 272-292.

Sriwongsitanont et al., (2011) "Effect of Freeze-Thawing Process on the Size and Lamellarity of PEG-Lipid Liposomes," The Open Colloid Science Journal 4: 1-6.

PCT/IL2023/050003, International Search Report, dated Mar. 31, 2023.

PCT/IL2023/050003, Written Opinion of the International Searching Authority, dated Mar. 31, 2023.

PCT/IL2023/050003, International Preliminary Report on Patentability (Chapter I), dated Jun. 20, 2024.

Blostein and Benderoff (1978) The use of radioiodinated albumin to measure internal and external vesicle space. Anal Biochem 84(1): 111-115.

*Primary Examiner* — Andrew S Rosenthal  
(74) *Attorney, Agent, or Firm* — Allan A. Fanucci, Esq.

(57) ABSTRACT

The present invention relates to a method of determining the trapped volume and the trapped aqueous volume of a plurality of liposomes in a liposomal composition. The method can be used for calculating the concentration of an active pharmaceutical ingredient entrapped within the liposomes and for quality assurance of a pre-formed liposomal composition.

20 Claims, 8 Drawing Sheets

DETERMINATION OF THE TRAPPED VOLUME OF A LIPOSOME

This application is a 371 filing of International Patent Application PCT/IL2023/050003 filed Jan. 1, 2023, which claims the benefit of U.S. provisional application No. 63/295,896 filed Jan. 2, 2022.

FIELD OF THE INVENTION

The present invention relates to a method of determining the trapped volume of a liposome and use thereof in liposome characterization.

BACKGROUND OF THE INVENTION

The trapped volume (Vt) and the trapped aqueous volume (Vtaq) of liposomes are important parameters in liposome characterization, particularly as they define the volume available for active pharmaceutical ingredient (API) encapsulation. Thus, determination of Vt and Vtaq enables to calculate the concentration of API encapsulated within liposomes in a liposomal composition. In compositions containing empty liposomes, the trapped volume and the trapped aqueous volume are important characteristics of the structure of the liposomes and their properties.

The trapped volume of liposomes can be determined using various methods, most of which involve measurement of a marker trapped inside the liposomes after removal of the untrapped marker. This approach may be suitable for all types of liposomes so long as the marker does not leak from the liposomes and a good separation between liposomes and extra-liposomal medium can be obtained. However, this approach requires the encapsulation of the marker during liposome preparation. Accordingly, it cannot be used to characterize batches designated for clinical use.

Oku et al. (Biochimica et Biophysica Acta (BBA)—Biomembranes, 691(2), 1982, 332-340) describe a method for determining the volume of the aqueous compartment of liposomes using the fluorescent dye, calcein. The fraction of the total volume that is within the liposomes is obtained as the fraction of the fluorescence that remains after adding cobalt(II) ions which, when chelated by calcein, quench its fluorescence.

Perkins et al. (Chemistry and Physics of Lipids, 64, 1993, 197-217) describe several methods to quantitate liposome captured volume. The first method utilized $^3H_2O$ and $^{14}C$-glucose to mark the total aqueous volume and external volume. This method relied on the difference in kinetics of membrane permeability of $^3H_2O$ compared to $^{14}C$-glucose. The method was performed at 4° C. in order to prevent glucose binding and permeation as well as reduce the risk of $^3H_2O$ vapor inhalation. The second method termed ViVo, was performed by adding the ESR spin probe 4-trimethyl-ammonium TEMPO (CAT1) to a total volume of 1 ml sample and then comparing the concentration of the probe in the supernatant above the centrifuged pellet to the concentration of probe in the total volume using a standard curve.

There is an unmet need for an accurate post-production measurement of the trapped volume of liposomes that can be used to characterize liposomal compositions suitable for clinical use.

SUMMARY OF THE INVENTION

The present invention discloses a post-production method of determining the trapped volume and trapped aqueous volume of liposomes, and use thereof in characterization and quality control of batch productions of liposomes for clinical use.

The present invention is based, in part, on the discovery of a simple, accurate, and reproducible method of determining the trapped volume and trapped aqueous volume of liposomes. The method utilizes a marker having a molecular weight of 1 kDa or higher that neither penetrates the liposomes nor becomes integrated in or associated with the lipid membrane thereby being present solely in the external aqueous phase. Upon separation of the liposomes from the suspending liquid (e.g. using centrifugation), an increase in the concentration of the marker in the liquid is measured as both the lipid membrane and the intra-liposomal aqueous medium occupy part of the dispersion volume but do not incorporate the marker. This increase in concentration is indicative of the trapped volume. Calculation of the trapped volume is based on the volume of the external aqueous medium deduced from the ratio of the signal induced by the marker in the suspending liquid following separation of the liposomes compared to the total signal before separation. In some embodiments, calculation may further be based on the determination of the signal induced by the marker in the suspending liquid and in the liposome-containing precipitate following separation compared to the total signal induced by the marker before separation.

Contrary to hitherto known methods which are either not suitable as post-production methods or utilize probes which permeate the lipid bilayer and are dependent on the zeta potential and surface charge of the liposomes, the method of the present invention is a post-production method which is sensitive, reproducible, and is less dependent on marker concentration, turbidity, quenching etc. It is also relatively easy and more accessible to perform.

According to a first aspect, there is provided a method of determining the trapped volume (Vt) and the trapped aqueous volume (Vtaq) of a plurality of liposomes in a liposomal composition, the method comprising the steps of:

(i) obtaining a liposomal composition comprising a plurality of liposomes at a predetermined concentration of lipids which are suspended or dispersed in a fluid medium;

(ii) adding a marker to said liposomal composition, wherein the marker is liposome impermeable and has a molecular weight equal to or higher than 1 kDa;

(iii) measuring a signal induced by the marker in said liposomal composition thereby determining the total volume of the liposomal composition;

(iv) separating the fluid medium from the plurality of liposomes thereby obtaining a fluid medium and a precipitate comprising a plurality of liposomes and an interstitial medium between the liposomes;

(v) measuring a signal induced by the marker in the separated fluid medium of step (iv) thereby determining the volume of the fluid medium and the interstitial medium;

(vi) optionally measuring a signal induced by the marker in the precipitate comprising a plurality of liposomes and an interstitial medium between the liposomes of step (iv) thereby determining the interstitial volume between the liposomes in the precipitate; and (vii) calculating the trapped volume (Vt) and the trapped aqueous volume (Vtaq) of the plurality of liposomes based on the volumes determined in steps (iii) and (v) or in steps (iii), (v), and (vi) and the predetermined concentration of step (i).

It is to be understood that when step (vi) is performed, step (vii) comprises calculating the trapped volume (Vt) and the trapped aqueous volume (Vtaq) of the plurality of liposomes based on the volumes determined in steps (iii), (v), and (vi) and the predetermined concentration of step (i).

According to another aspect, there is provided a method of determining the trapped volume (Vt) and the trapped aqueous volume (Vtaq) of a plurality of liposomes in a liposomal composition, the method comprising the steps of:

(i) obtaining a liposomal composition comprising a plurality of liposomes at a predetermined concentration of lipids which are suspended or dispersed in a fluid medium;

(ii) adding a marker to said liposomal composition, wherein the marker is liposome impermeable and has a molecular weight equal to or higher than 1 kDa;

(iii) measuring a signal induced by the marker in said liposomal composition thereby determining the total volume of the liposomal composition;

(iv) separating the fluid medium from the plurality of liposomes thereby obtaining a fluid medium and a precipitate comprising a plurality of liposomes and an interstitial medium between the liposomes;

(v) measuring a signal induced by the marker in the separated fluid medium of step (iv) thereby determining the volume of the fluid medium and the interstitial medium; and (vi) calculating the trapped volume (Vt) and the trapped aqueous volume (Vtaq) of the plurality of liposomes based on the volumes determined in steps (iii) and (v) and the predetermined concentration of step (i).

It is to be understood that calculating the trapped volume (Vt) and the trapped aqueous volume (Vtaq) of the plurality of liposomes based on the volumes determined in steps (iii) and (v) comprises calculating the ratio between the signal of the marker in the separated fluid medium following step (iv) and its signal in the liposomal composition prior to step (iv).

According to yet another aspect, there is provided a method of determining the trapped volume (Vt) and the trapped aqueous volume (Vtaq) of a plurality of liposomes in a liposomal composition, the method comprising the steps of:

(i) obtaining a liposomal composition comprising a plurality of liposomes at a predetermined concentration of lipids which are suspended or dispersed in a fluid medium;

(ii) adding a marker to said liposomal composition, wherein the marker is liposome impermeable and has a molecular weight equal to or higher than 1 kDa;

(iii) measuring a signal induced by the marker in said liposomal composition thereby determining the total volume of the liposomal composition;

(iv) separating the fluid medium from the plurality of liposomes thereby obtaining a fluid medium and a precipitate comprising a plurality of liposomes and an interstitial medium between the liposomes;

(v) measuring a signal induced by the marker in the separated fluid medium of step (iv) thereby determining the volume of the fluid medium and the interstitial medium;

(vi) measuring a signal induced by the marker in the precipitate comprising a plurality of liposomes and an interstitial medium between the liposomes of step (iv) thereby determining the interstitial volume between the liposomes in the precipitate; and (vii) calculating the trapped volume (Vt) and the trapped aqueous volume (Vtaq) of the plurality of liposomes based on the volumes determined in steps (iii), (v), and (vi) and the predetermined concentration of step (i).

In one embodiment, determination of the trapped volume (Vt) and the trapped aqueous volume (Vtaq) comprises determination of the specific trapped volume and the specific trapped aqueous volume, respectively.

According to some embodiments, the marker is water soluble. According to other embodiments, the marker has a molecular weight of at least about 2 kDa. In certain embodiments, the marker is a radioactive marker. In particular embodiments, the marker is inulin. In other particular embodiments, the marker is $^{14}$C-carboxy inulin.

In further embodiments, the signal induced by the marker is measured using at least one technique selected from radiation detection, calorimetry, fluorescence, High Performance Liquid Chromatography (HPLC), Liquid Chromatography combined with mass spectrometry (LC/MS), Gas-Chromatography (GC), GC-lined Mass-Spectrometry (GC-MS), Infrared spectroscopy, Raman spectroscopy, NMR, colorimetry, UV-VIS spectroscopy, and combinations thereof. Each possibility represents a separate embodiment.

In various embodiments, the liposomal composition comprises a plurality of liposomes selected from the group consisting of unilamellar vesicles (SUV), large unilamellar vesicles (LUV), giant unilamellar vesicles (GUV), oligolamellar vesicles (OLV), multilamellar vesicles (MLV), multivesicular liposomes (MVL), and a mixture or combination thereof. Each possibility represents a separate embodiment.

In certain embodiments, the liposomal composition comprises a plurality of liposomes in sizes ranging from about 0.3 µm to about 50 µm, including each value within the specified range. In other embodiments, the liposomal composition comprises a plurality of liposomes in sizes ranging from about 1 µm to about 40 µm, including each value within the specified range.

In various embodiments, the liposomal composition comprises a plurality of liposomes having a lipid concentration of about 50 mM to about 200 mM, including each value within the specified range. In particular embodiments, the liposomal composition comprises a plurality of liposomes having a lipid concentration of about 100 mM to about 150 mM, including each value within the specified range.

In some embodiments, the liposomal composition comprises a plurality of empty liposomes essentially free of an active pharmaceutical ingredient. In other embodiments, the liposomal composition comprises a plurality of liposomes encapsulating an active pharmaceutical ingredient. In accordance with the latter embodiments, the method of the present invention further comprises determining the concentration of the active pharmaceutical ingredient encapsulated by the plurality of liposomes.

In various embodiments, separating the fluid medium from the plurality of liposomes is performed by centrifugation, filtration, or decantation. Each possibility represents a separate embodiment. In one embodiment, separating the fluid medium from the plurality of liposomes provides a fluid medium which is substantially devoid of liposomes.

In a currently preferred embodiment, separating the fluid medium from the plurality of liposomes is performed by centrifugation.

In some embodiments, centrifugation of the liposomal composition is performed at a relative centrifugal force of about 10,000 to about 30,000 (×g), including each value within the specified range.

In further embodiments, centrifugation of the liposomal composition is performed at a temperature of about 2° C. to about 25° C., including each value within the specified range.

In additional embodiments, centrifugation of the liposomal composition is performed for a time period in the range of about 10 minutes to about 100 minutes, including each value within the specified range.

In various embodiments, the method disclosed herein is useful in controlling the quality of a liposomal composition. In accordance with these embodiments, the method further comprises comparing the determined trapped volume (Vt) and trapped aqueous volume (Vtaq) with reference trapped volume (Vt) and trapped aqueous volume (Vtaq) values, and rejecting said liposomal composition if the determined trapped volume (Vt) and trapped aqueous volume (Vtaq) differ from the reference values by more than plus or minus 10%.

In other embodiments, the method disclosed herein is useful in controlling the quality of a liposomal composition comprising an active pharmaceutical ingredient (API) encapsulated within a plurality of liposomes, the method comprising determining the concentration of API encapsulated within a plurality of liposomes in a liposomal composition from the trapped volume (Vt) and trapped aqueous volume (Vtaq) as disclosed herein, comparing the determined API concentration with a reference API concentration, and rejecting said liposomal composition if the determined API concentration differs from the reference API concentration by more than plus or minus 10%.

According to some embodiments, there is provided a liposomal composition formulated for intra-articular administration comprising a polyol tonicity agent; and a plurality of liposomes consisting essentially of 1,2-Dimyristoyl-sn-Glycero-3-Phosphocholine (DMPC), and 1,2-Dipalmitoyl-sn-Glycero-3-Phosphocholine (DPPC) at a ratio of about 45:55, wherein the composition is essentially free of an active pharmaceutical agent, and wherein the plurality of liposomes are characterized by a specific trapped aqueous volume in the range of about 1 to about 4 µl/mg lipid, including each value within the specified range, as determined by any one of the methods disclosed herein.

According to another aspect, there is provided a liposomal composition formulated for intra-articular administration comprising a fluid medium; a polyol tonicity agent; and a plurality of liposomes consisting essentially of 1,2-Dimyristoyl-sn-Glycero-3-Phosphocholine (DMPC), and 1,2-Dipalmitoyl-sn-Glycero-3-Phosphocholine (DPPC) at a ratio of about 45:55, wherein the composition is essentially free of an active pharmaceutical agent, and wherein the plurality of liposomes are characterized by a specific trapped aqueous volume in the range of about 1 to about 4 µl/mg lipid, including each value within the specified range, as determined by a method comprising the steps of:

(i) adding a marker to said liposomal composition, wherein the marker is liposome impermeable and has a molecular weight equal to or higher than 1 kDa;

(ii) measuring a signal induced by the marker in the liposomal composition thereby determining the total volume of the liposomal composition;

(iii) determining the volume of the fluid medium and the interstitial medium between liposomes obtained by separating the fluid medium from the plurality of liposomes and measuring a signal induced by the marker in the fluid medium following separation; and (iv) calculating the trapped volume (Vt) and trapped aqueous volume (Vtaq) of the plurality of liposomes based on the volumes determined in steps (ii) and (iii) and the concentration of the lipids forming the liposomes.

According to various embodiments, step (iii) of determining the volume of the fluid medium and the interstitial medium between liposomes further comprises determining the interstitial volume between liposomes in a precipitate by measuring a signal induced by the marker in the precipitate following separation from the fluid medium. In one embodiment, separation is performed by centrifugation.

According to some embodiments, the fluid medium comprises a histidine buffer. According to other embodiments, the polyol is a linear polyol. According to yet other embodiments, the polyol is selected from the group consisting of mannitol, dextrose, lactose, trehalose, and combinations thereof. Each possibility represents a separate embodiment. According to particular embodiments, the polyol is mannitol. According to various embodiments, the weight ratio between the plurality of liposomes and the polyol tonicity agent ranges from about 6:1 to about 2:1, including all iterations of ratios within the specified range.

According to further embodiments, the plurality of liposomes consists essentially of a combination of DMPC and DPPC, wherein DMPC is present in a weight percent ranging from about 1% (w/w) to about 10% (w/w) and DPPC is present in a weight percent ranging from about 2% (w/w) to about 12% (w/w), including each value within the specified ranges. According to certain embodiments, the liposomal composition has a pH in the range of about 5 to about 8, including each value within the specified range. According to other embodiments, the plurality of liposomes are characterized by a specific trapped aqueous volume of about 1.5 to about 3.5 µl/mg lipid, including each value within the specified range. According to yet other embodiments, the plurality of liposomes are characterized by a specific trapped aqueous volume of about 2 to about 3 µl/mg lipid, including each value within the specified range. According to further embodiments, the plurality of liposomes are characterized by a trapped aqueous volume of about 10% to about 35%, including each value within the specified range. According to additional embodiments, the plurality of liposomes are characterized by a trapped aqueous volume of about 20% to about 30%, including each value within the specified range.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. These exemplary methods and/or materials are not intended to be necessarily limiting.

F—305 mM lipid; G—10 mM NaCl; H—100 mM NaCl; I—150 mM NaCl; J—3000 mM NaCl; K—MLVs; L—LMVVs; and M—MLVs.

Figure 4:
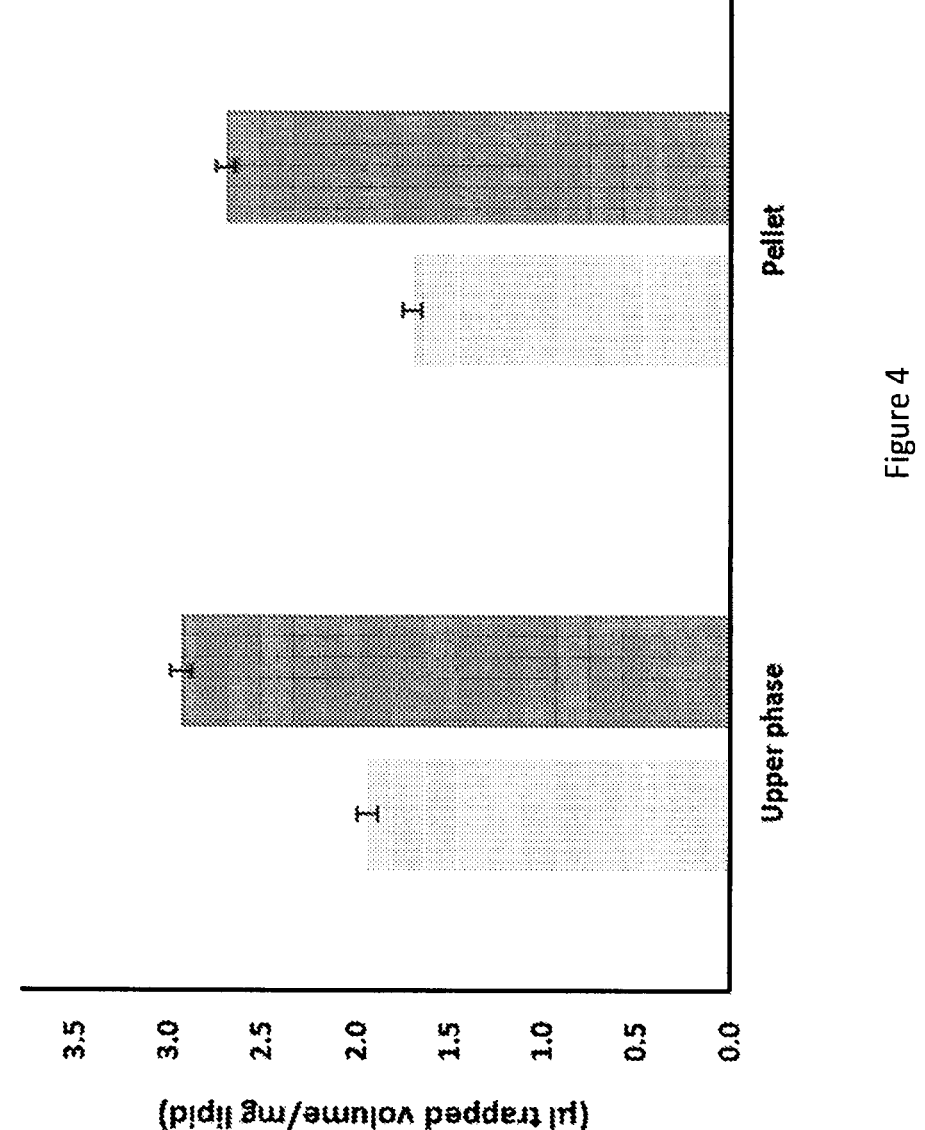

FIG. 4 is a diagram showing the specific trapped aqueous volume (light gray) and specific trapped volume (dark gray) as determined using the supernatant and total volume (left) and supernatant and pellet (right).

Figure 5:
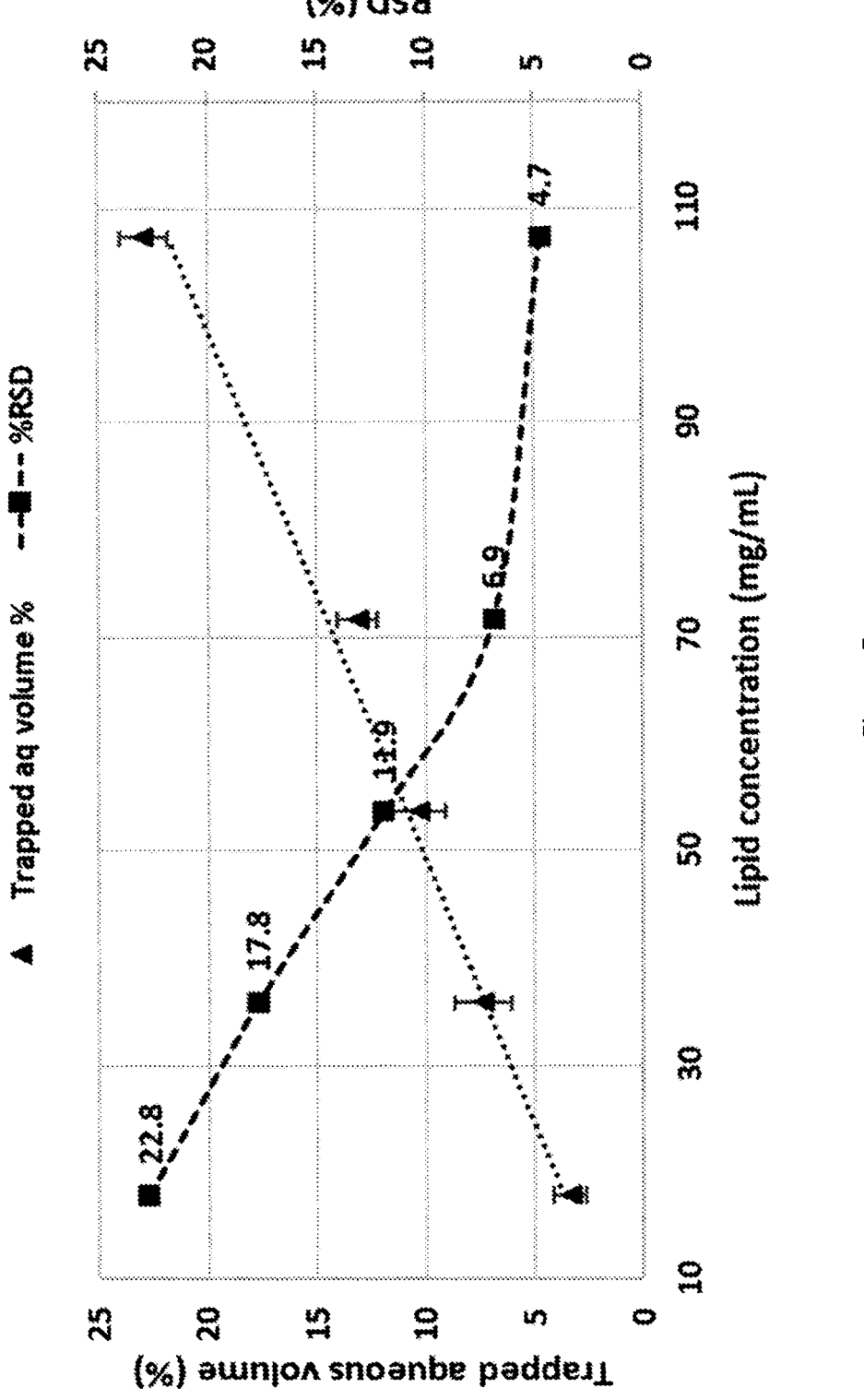

FIG. 5 is a graph showing the % trapped aqueous volume and % RSD at different lipid concentrations. The results obtained are based on the radioactivity of the supernatant (n=3).

Figure 6:
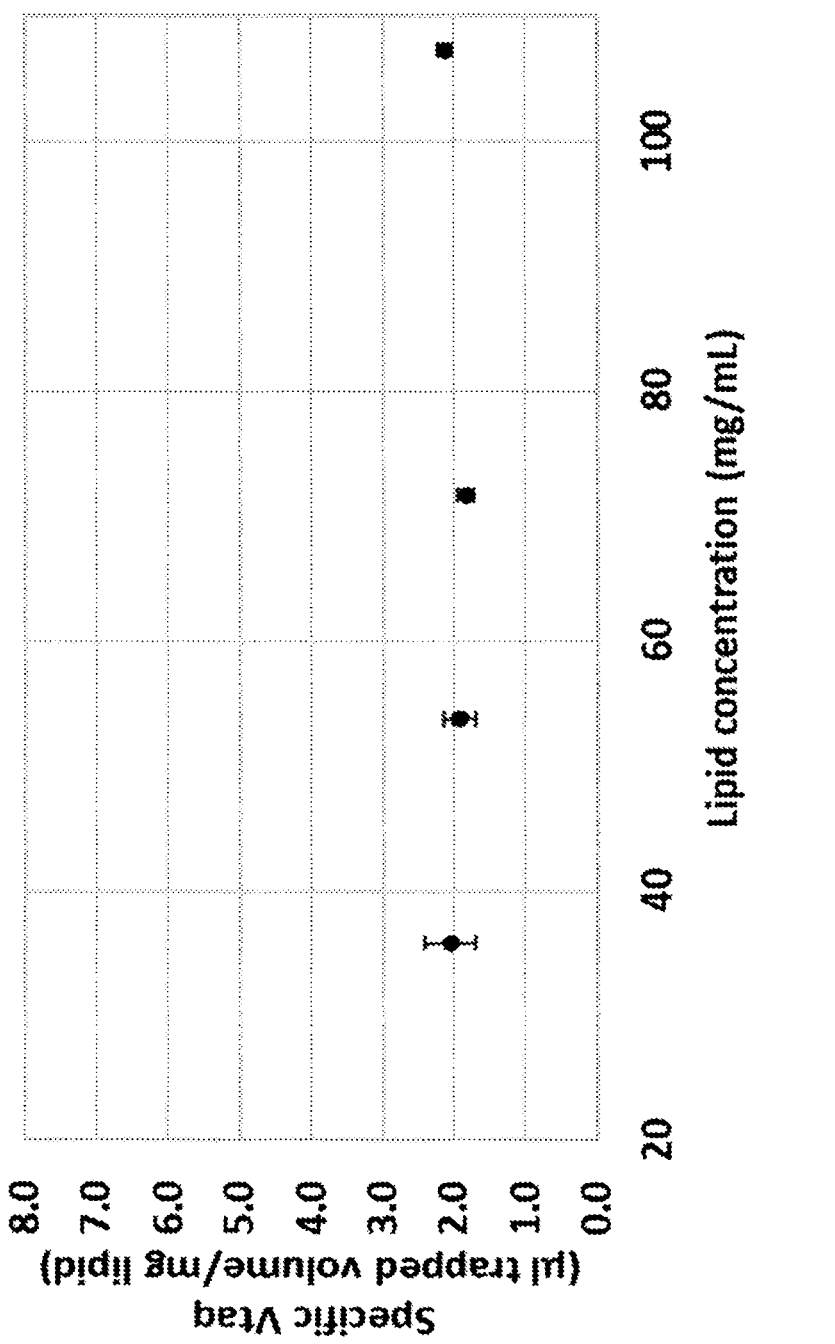

FIG. 6 is a graph showing the specific trapped aqueous volume (μl trapped volume/mg lipid) vs. lipid concentration. The average specific trapped aqueous volume was 2±0.1 μl per mg lipid (n=15).

Figure 7:
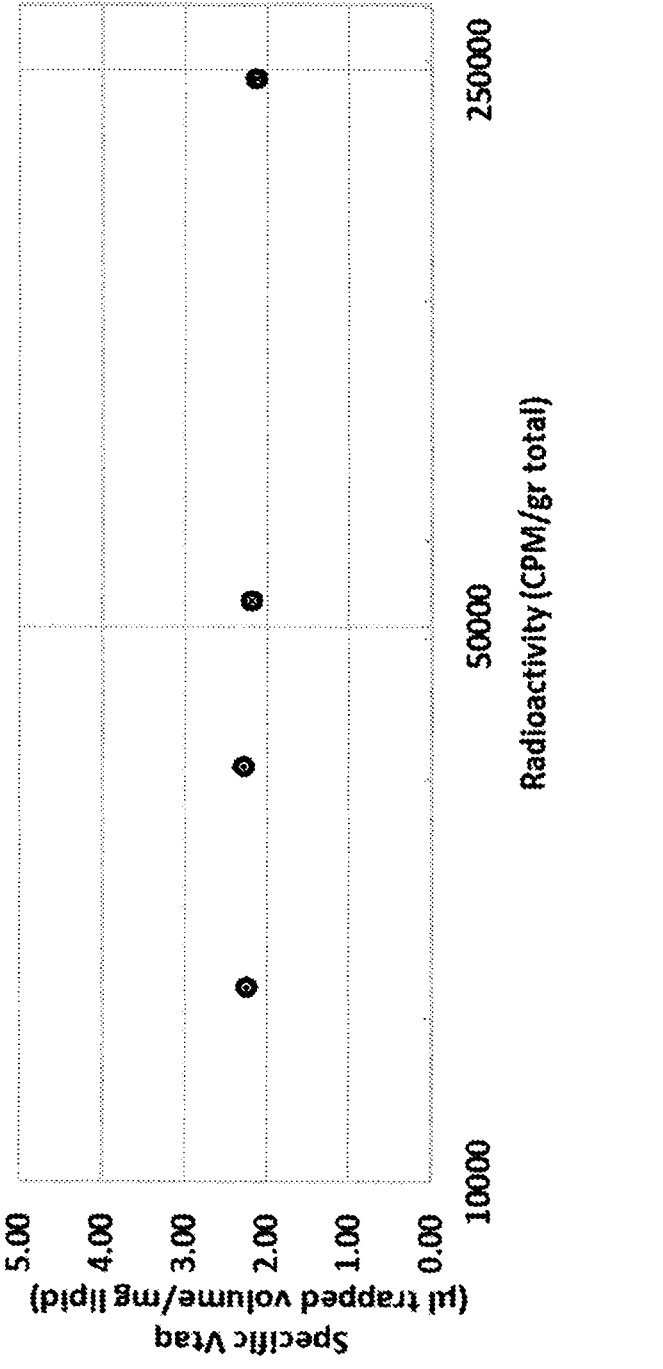

FIG. 7 is a graph showing the specific trapped aqueous volume at different $^{14}$C-carboxy-inulin concentrations (CPM normalized to total sample weight).

Figure 8:
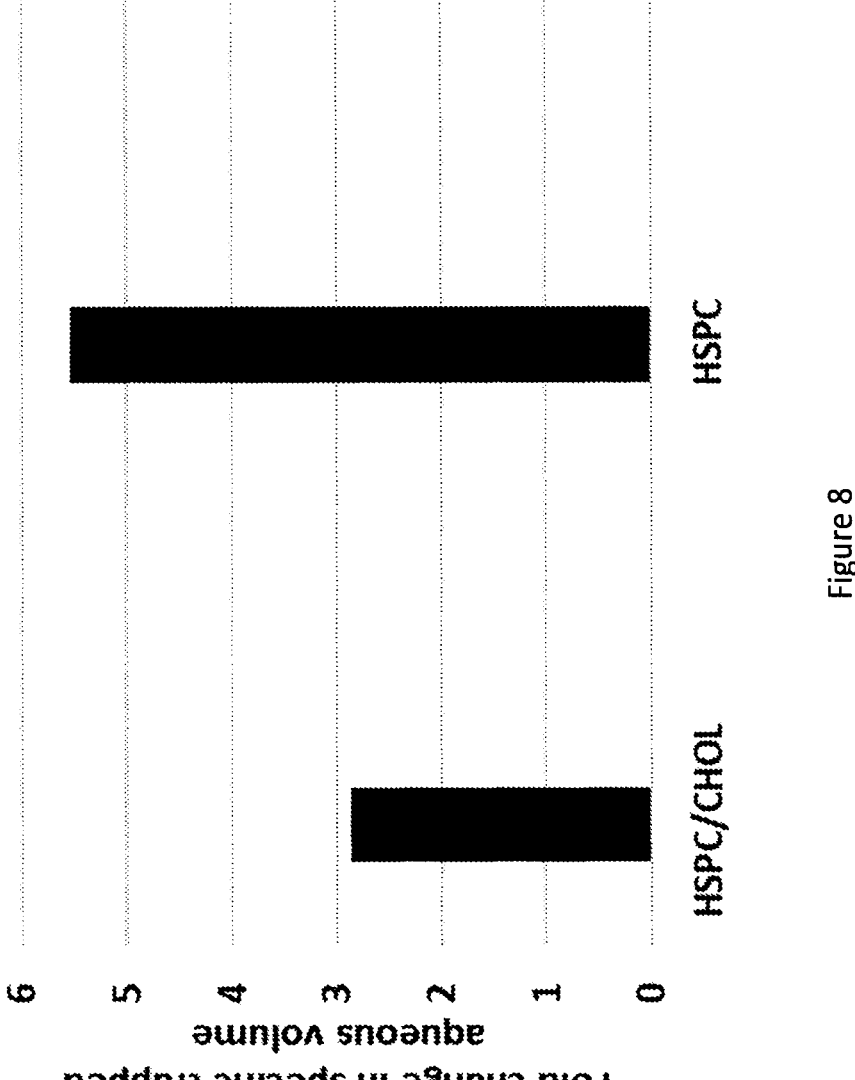

FIG. 8 is a diagram indicating the fold change in specific trapped aqueous volume of a liposomal composition containing HSPC and cholesterol or HSPC alone (n=2).

DETAILED DESCRIPTION OF THE INVENTION

The present invention relates to a method of determining the trapped volume (Vt) and the trapped aqueous volume (Vtaq) of a liposomal composition in a non-destructive manner. The method can be used to control the quality of production of liposomal compositions with improved accuracy and reproducibility.

While the currently used methods of determining the trapped volumes of liposomes require encapsulating markers within liposomes, the present invention defines a different approach. This approach utilizes a marker which is liposome impermeable having a molecular weight≥1 kDa, such as the radioactive marker $^{14}$C-carboxy-inulin. When using a marker that cannot cross the lipid membrane, it is distributed only in the liposomal external aqueous phase. Upon separation of the fluid medium from the liposomes (e.g. using centrifugation), precipitation of the liposomes occurs such that there are substantially no liposomes remaining in the supernatant. The concentration of the marker in the supernatant can be measured to calculate the volume of the external aqueous phase. The subtraction of the volume of the external aqueous phase including the interstitial volume between liposomes and the calculated lipid volume from the total volume of the liposomal composition corresponds to the liposome trapped volume.

This method overcomes the limitations of previously described approaches since it is a post-production method that can be utilized on a small fraction of already formed liposomes and does not involve the encapsulation of the marker within the liposomes that renders them unsuitable for clinical use. Also, when using a captured marker to determine the trapped volume, a uniform distribution of the marker in all aqueous compartments is required. However, it is known that in multilamellar vesicles (MLV), a captured solute is not always distributed evenly due to the differences between solute and water permeability. The method disclosed herein provides an accurate measurement of the trapped volume of various liposomes including MLVs and can be performed without altering the liposome structures. The method utilizes high molecular weight polar markers that do not permeate the lipid bilayer thereby providing accurate and reproducible measurement of the trapped volume and trapped aqueous volume. The method of the present invention can be used for quality control and physical assessment of batch productions of empty and API-loaded liposomes.

Some embodiments of the invention are described herein with reference to the accompanying figures. The description, together with the figures, makes apparent to a person having ordinary skill in the art how some embodiments may be practiced. The figures are for the purpose of illustrative description and no attempt is made to show structural details of an embodiment in more detail than is necessary for a fundamental understanding of the invention. For the sake of clarity, some objects depicted in the figures are not to scale.

The present invention provides a method of determining the trapped volume (Vt) and the trapped aqueous volume (Vtaq) of a plurality of liposomes in a liposomal composition comprising several steps, some of which can be performed sequentially at any order or simultaneously, with each possibility representing a separate embodiment. As used herein, the term "trapped volume" refers to the sum of the volume occupied by the lipid membrane constituting the liposomes and the volume of the intra-liposomal aqueous medium. In some aspects and embodiments, the method disclosed herein comprises the determination of the trapped aqueous volume. As used herein, the term "trapped aqueous volume" refers to the volume of the intra-liposomal aqueous medium. In further aspects and embodiments, the method of the present invention provides the determination of the specific trapped volume and specific trapped aqueous volume which are the trapped volume and trapped aqueous volume, respectively, normalized by the weight of the lipids.

As used herein, the term "a liposome" refers to a vesicle characterized by an inner aqueous center surrounded by a lipid membrane typically comprising phospholipid bilayer(s). Exemplary phospholipids include, but not limited to, phosphatidylcholine (PC), phosphatidylethanolamine, phosphatidylinositol, phosphatidylserine, phosphatidylglycerol, diphosphatidylglycerols or any derivatives or combinations thereof. Each possibility represents a separate embodiment. Suitable phosphatidylcholines within the scope of the present invention include, but are not limited to, 1,2-dimyristoyl-sn-glycero-3-phosphocholine (DMPC), 1,2-dipalmitoyl-sn-glycero-3-phosphocholine (DPPC), 1,2-distearoyl-sn-glycero-3-phosphocholine (DSPC), 1,2-diolcoyl-sn-glycero-3-phosphocholine (DOPC), 1,2-dilauroyl-sn-glycero-3-phosphocholine (DLPC), 1-palmitoyl-2-olcoyl-sn-glycero-3-phosphocholine (POPC), and a mixture or combination thereof. Each possibility represents a separate embodiment. Suitable phosphatidylethanolamines include, but are not limited to, 1,2-dilauroyl-L-phosphatidyl-ethanolamine (DLPE), 1,2-dioleoyl-sn-glycero-3-phosphoethanolamine (DOPE), 1,2-diphytanoyl-sn-glycero-3-phospho-ethanolamine (DPhPE), 1,3-dipalmitoyl-sn-glycero-2-phosphoethanolamine (1,3-DPPE), 1-palmitoyl-3-oleoyl-sn-glycero-2-phosphoethanolamine (1,3-POPE), biotin-phosphatidylethanolamine, 1,2-dimyristoyl-sn-glycero-3-phosphoethanolamine (DMPE), dipalmitoylphosphatidylethanolamine (DPPE), 1,2-distearoyl-sn-glycero-3-phosphoethanolamine (DSPE), and a mixture or combination thereof. Each possibility represents a separate embodiment. Suitable phosphatidylglycerols include, but are not limited to, 1,2-dimyristoyl-sn-glycero-3-(phospho-rac-(1-glycerol)) (DMPG), 1,2-dipalmitoyl-sn-glycero-3-phosphoglycerol (DPPG), 1,2-distearoylphosphatidylglycerol (DSPG), and a mixture or combination thereof. Each possibility represents a separate embodiment.

According to the principles of the present invention, the method disclosed herein may be used to determine the trapped volume of liposomes having structures that include unilamellar vesicles (SUV), large unilamellar vesicles (LUV), giant unilamellar vesicles (GUV), oligolamellar vesicles (OLV), multilamellar vesicles (MLV), multivesicular liposomes (MVL), and a mixture or combination thereof. Each possibility represents a separate embodiment.

The method of the present invention can be performed on empty liposomes, or it can be performed on liposomes encapsulating an active pharmaceutical ingredient (API). Each possibility represents a separate embodiment. Since the marker according to the principles of the present invention is not uptaken by the liposomes, the presence of an active pharmaceutical ingredient encapsulated within the liposomes does not interfere with the trapped volume determination. Due to the correlation between the trapped volume and the concentration of the active pharmaceutical ingredient encapsulated within the liposomes, determination of the API concentration can be obtained. Accordingly, the determination of the trapped volume of the liposomes enables to assess the concentration of the active pharmaceutical ingredient encapsulated therein. Thus, the present invention further provides a method of determining the concentration of an active pharmaceutical ingredient encapsulated within a plurality of liposomes in a liposomal composition comprising determining the trapped volume and/or trapped aqueous volume of the plurality of liposomes encapsulating an active pharmaceutical ingredient according to the methods disclosed herein.

In some aspects and embodiments, the method of the present invention utilizes a liposomal composition comprising a fluid medium and a plurality of liposomes at a predetermined concentration of lipids typically expressed in weight unites. The term "a liposomal composition" as used herein refers to a composition comprising a plurality of liposomes suspended or dispersed in a suitable liquid medium, for example an aqueous medium such as a buffer. When referring to a liposomal composition, it is to be understood that it includes a reference to a portion of said composition sampled in order to afford information on the trapped volume of the entire composition. Typically, the concentration of lipids in the liposomal composition is in the range of about 50 mM to about 200 mM, including each value within the specified range. Exemplary concentration ranges included within the scope of the present invention are about 50 mM to about 150 mM, about 50 mM to about 100 mM, and about 100 mM to about 200 mM, including each value within the specified ranges. According to the principles of the present invention, the concentration of the lipids in the liposomal composition enables to determine the volume occupied by the liposome lipid membrane in the composition. The volume of lipids can be calculated by dividing the weight of the lipids by their density. Typically, the density of the lipids forming the liposome membrane can be measured using a suitable density meter (for example an Anton Paar density meter). Alternatively, the density can be obtained from a reference sample or calculated according to various models.

In certain aspects and embodiments, a marker having a molecular weight equal to or higher than 1 kDa is then added to the composition. According to the principles of the present invention, the marker is a compound which is not internalized by the liposomes nor does it interact with the liposomal membrane thereby being liposome impermeable. According to some embodiments, the marker is a polar molecule which is preferably water soluble. Markers within the scope of the present invention include compounds comprising detectable moieties which induce a signal that can be measured and quantified by known techniques such as spectral measurements. Suitable markers include, but are not limited to, radioactive agents, chromophores, fluorescent compounds, phosphorescent compounds, magnetic compounds, and heavy metal clusters. Each possibility represents a separate embodiment. An exemplary marker is a radioactive marker which comprises radioactive isotopes that emit radiation as the signal that can be measured. An additional exemplary marker is a fluorescent compound which emits light at a specific wavelength during exposure to radiation from an external source, said emitted light can be used as a signal that can be measured. The signal induced by the marker can be measured as is known in the art, for example using various detectors and monitors. Techniques that can be utilized for measuring the signal include, but are not limited to radiation detection, calorimetry, fluorescence, High Performance Liquid Chromatography (HPLC), Liquid Chromatography combined with mass spectrometry (LC/MS), Gas-Chromatography (GC), GC-lined Mass-Spectrometry (GC-MS), Infrared spectroscopy, Raman spectroscopy, NMR, colorimetry, UV-VIS spectroscopy, and combinations thereof. Each possibility represents a separate embodiment.

According to the principles of the present invention, the markers comprise compounds having a molecular weight of at least 1 kDa, preferably at least 2 kDa. Typically, the molecular weight of the marker ranges from 1 kDa to 1,000 kDa, including each value within the specified range. Exemplary molecular weights of the marker include, but are not limited to, 1 kDa, 2 kDa, 3 kDa, 4 kDa, 5 kDa, 6 kDa, 7 kDa, 8 kDa, 9 kDa, 10 kDa, 15 kDa, 20 kDa, 25 kDa, 30 kDa, 35 kDa, 40 kDa, 45 kDa, 50 kDa, 55 kDa, 60 kDa, 65 kDa, 70 kDa, 75 kDa, 80 kDa, 85 kDa, 90 kDa, 95 kDa, 100 kDa, 150 kDa, 200 kDa, 250 kDa, 300 kDa, 350 kDa, 400 kDa, 450 kDa, 500 kDa, 550 kDa, 600 kDa, 650 kDa, 700 kDa, 750 kDa, 800 kDa, 850 kDa, 900 kDa, 950 kDa, or 1,000 kDa. Each possibility represents a separate embodiment.

In some aspects and embodiments, the markers comprise polysaccharides including, but not limited to, inulin, FITC-inulin, dextran, FITC-dextran, and derivatives thereof. Each possibility represents a separate embodiment. In other aspects and embodiments, the markers comprise carbohydrates, polypeptides or synthetic polymers such as, but not limited to, polyvinyl pyrrolidone, polyvinyl alcohol, polyethylene glycol, horseradish peroxidase (HRP), and the like. Each possibility represents a separate embodiment. While the markers within the scope of the present invention typically have a molecular weight of at least 1 kDa, it is to be understood that markers having a molecular weight that is lower than 1 kDa that do not penetrate the liposomes or become integrated in or associated with the lipid membrane are also contemplated to afford the accurate measurement of the trapped volume according to the principles of the present invention. Such markers include, but are not limited to, di-, tri- and oligo-saccharides such as sucrose and the like.

In some currently preferred aspects and embodiments, radioactive markers are used in the methods of the present invention. Exemplary radioactive markers within the scope of the present invention include, but are not limited to, $^{14}$C-carboxyl-inulin, $^{125}$I-polyvinyl pyrrolidone, and radioactive carbohydrates. Each possibility represents a separate embodiment. Since the radioactive marker, such as $^{14}$C-carboxyl-inulin, does not interact with the liposomes, it can be added in concentrations of about 0.1 micro curie (μci)/ml to about 10 μci/ml, including each value within the specified range. Exemplary concentration ranges included within the scope of the present invention are about 0.1 μci/ml to about 5 µci/ml, about 0.5 µci/ml to about 5 µci/ml, and about 0.5 µci/ml to about 3 µci/ml, including each value within the specified ranges.

According to the principles provided herein, the marker is not available for the intra-liposomal volume. Thus, mixing it with a liposomal composition results in its increased concentration in the extra-liposomal medium. In some aspects and embodiments, the method of the present invention comprises measuring the signal induced by the marker in the liposomal composition. For example, when using a radioactive marker, the method comprises measuring the radioactivity/weight (disintegration per minute (DPM)/gr), of the total liposome composition. Since the density of the phospholipids used is very close to 1 (less than 1.05), for such liposomes the radioactivity/weight is substantially interchangeable with the radioactivity/volume (DPM/ml). By determining the (DPM/ml) of the total liposome dispersion, $(DPM/ml)_{total}$, the volume of the liposomal composition is determined.

Measuring radioactivity can be performed as is known in the art, for example using a suitable liquid Scintillation Counter such as Packard 1900 TR Scintillation Counter, Packard Tri-Carb liquid scintillation counter, and the like.

Following determination of the volume occupied by the entire liposomal composition, the fluid medium is separated from the plurality of liposomes. Separation of the fluid medium from the plurality of liposomes can be performed as is known in the art, for example by centrifugation, filtration or decantation. Each possibility represents a separate embodiment. Typically, the liposomal composition supplemented with the marker is centrifuged to precipitate the plurality of liposomes. According to the principles of the present invention, centrifugation is performed such that the supernatant solution is substantially devoid of liposomes. Typically, liposomes in sizes ranging from about 0.3 µm to about 50 µm, for example in the range of from about 1 µm to about 40 µm, are capable of being precipitated upon sufficient centrifugation. In some embodiments, where the composition comprises small liposomes, ultracentrifugation should be used to achieve a complete precipitation. In some aspects and embodiments, centrifugation of the liposomal composition is performed at a relative centrifugal force of about 10,000 to about 30,000 (×g), including each value within the specified range. Exemplary relative centrifugal forces include, but are not limited to, about 10,000, about 11,000, about 12,000, about 13,000, about 14,000, about 15,000, about 16,000, about 17,000, about 18,000, about 19,000, about 20,000, about 21,000, about 22,000, about 23,000, about 24,000, about 25,000, about 26,000, about 27,000, about 28,000, about 29,000, or about 30,000 (×g), with each possibility representing a separate embodiment. Although centrifugation may be performed at room temperatures, centrifugation at lower temperatures is also contemplated within the scope of the present invention. Typically, centrifugation is performed at a temperature range of about 2° C. to about 25° C., including each value within the specified range. Exemplary temperatures include, but are not limited to, about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C. about 24° C., or about 25° C., with each possibility representing a separate embodiment. Typically, centrifugation for a time period in the range of about 10 minutes to about 100 minutes at the aforementioned relative centrifugal forces is sufficient to afford a supernatant which is substantially devoid of liposomes. Exemplary time periods for centrifugation include, but are not limited to, about 10, about 20, about 30, about 40, about 50, about 60, about 70, about 80, about 90, or about 100 minutes, with each possibility representing a separate embodiment.

Following centrifugation and substantially complete precipitation of the liposomes, the supernatant is collected and the signal induced by the marker is measured thereby enabling the determination of the volume of the extra-liposomal medium (supernatant or separated fluid medium plus the interstitial volume present between the precipitated liposomes). For example, when a radioactive marker is used, radioactivity of the supernatant $(DPM/ml)_{sup}$ is measured. According to the principles of the present invention, $(DPM/ml)_{sup}$ represents the radioactivity/ml of the extra-liposome medium, namely the volume of the supernatant and the volume of the interstitial (trapped between the liposomes) extra-liposome medium of the precipitate. Therefore, in cases where the radioactive tracer is added to the liposome dispersion after the liposomes were formed, the ratio between $(DPM/ml)_{total}$ and $(DPM/ml)_{sup}$ is used to determine the entire aqueous volume exterior to the liposomes $(V_{free}$, equation 1).

Figure 1:
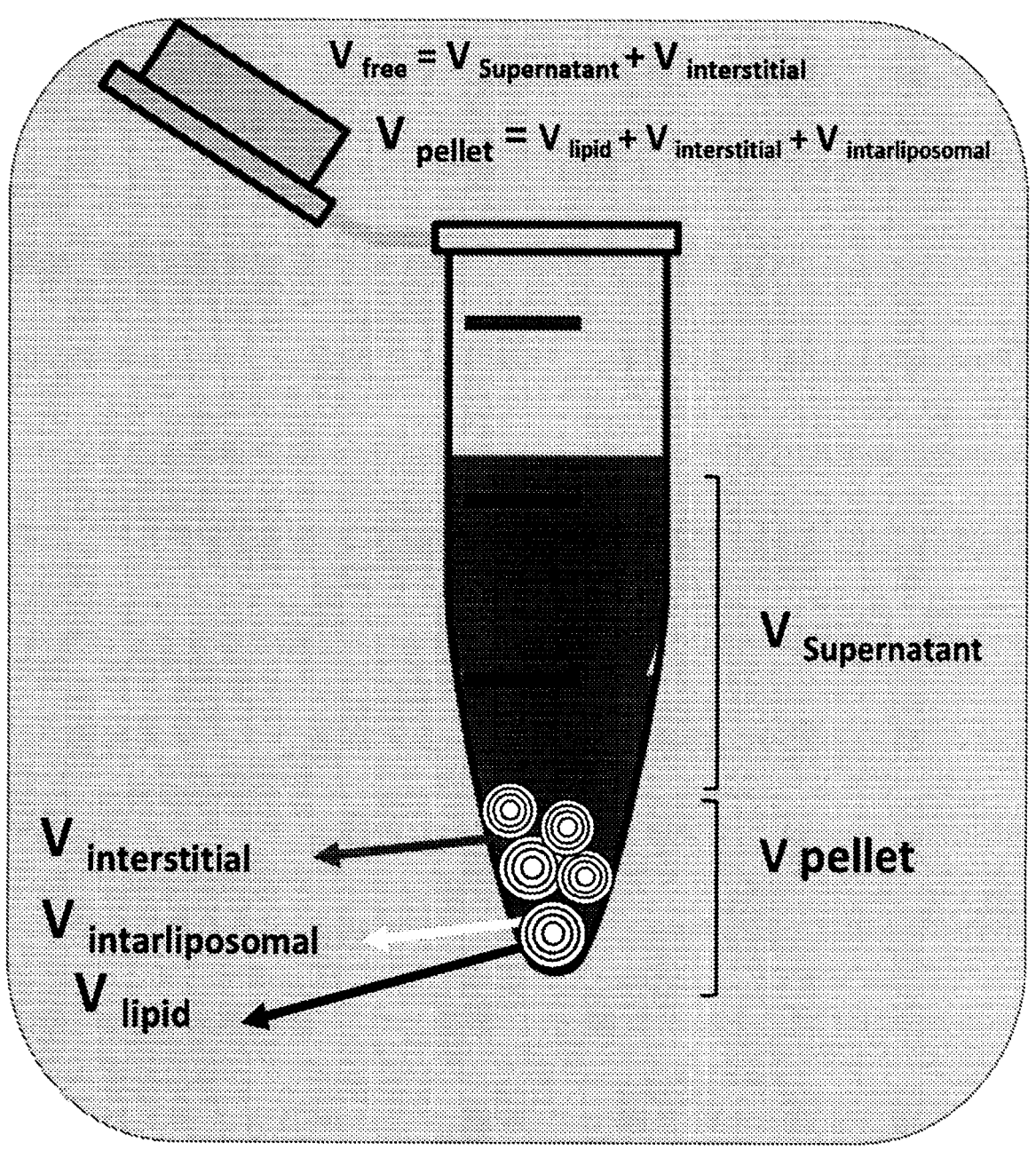
FIG. 1 is a schematic illustration of an Eppendorf vial following centrifugation indicating the different volumes used for calculating the trapped volume according to certain embodiments of the present invention.

The liposomal trapped volume (Vt) is then determined by subtracting the volume exterior to the liposomes from the total volume of the dispersion (equation 2). The trapped aqueous volume (Vtaq) is calculated by subtracting the volume of the liposome lipids $(V_{lipids})$ from the liposomal trapped volume (equation 3). $V_{lipids}$ is determined from the known liposome lipid weight and the known lipid density. The ratio of Vt or Vtaq to lipids used to prepare the liposomes describes the specific Vt and specific Vtaq, respectively. These are the most relevant descriptors of liposomes in a liposome dispersion. An illustration of an Eppendorf test tube with the definition of the different volumes occupied by each of the components (lipid, free (non-liposomal volume which also includes the interstitial volume) and intra-liposome aqueous phase (Vtaq) is shown in FIG. 1.

$$1.\ V\ free = V\ Supernatant + V\ interstitial = \frac{\left(\frac{DPM}{ml}\right)total}{\left(\frac{DPM}{ml}\right)upper}$$

$$2.\ Vt = Vtotal - Vfree$$

$$3.\ Vtaq = Vt - Vlipids$$

Optionally, the signal induced by the marker in the precipitate which comprises a plurality of liposomes and an interstitial medium between the liposomes can further be measured and used to determine the interstitial volume between the liposomes in the precipitate.

Within the scope of the present invention is the use of the determined Vt and Vtaq as well as the specific Vt and specific Vtaq, as descriptors of the quality of a dispersion containing liposomes. In accordance with these embodiments, the methods of the present invention further comprise comparing the determined trapped volume with reference trapped volume values and rejecting said liposomal composition if the determined trapped volume differs from the reference trapped volume values by more than plus or minus 10%. When the determined trapped volume is compared with reference trapped volume values it can be compared with a standard trapped volume known to be acceptable for clinical use. The standard trapped volume may be a precise figure, or it may be a range. For example, it may be an absolute amount with an acceptable percentage deviation i.e. ±10%, ±5%, etc. A calculated trapped volume can be compared to a standard trapped volume range and, if it falls outside the range by more than plus or minus 10%, the liposomal composition is rejected. Typically, the reference trapped volume values correspond to a range of values that are acceptable according to the specifications of the liposomal composition and a rejection occurs where the difference corresponds to values which are either lower by more than 10% from the lower end of the range or higher by more than 10% from the upper end of the range. Typical standard trapped volumes of a liposomal composition may be, for example, between about 0.1 to about 10 μl/mg lipid, between about 0.3 to about 5 μl/mg lipid, or between about 1 to about 4 μl/mg lipid etc., including each value within the specified ranges. The standard trapped volume may be obtained from a control sample that can be determined before, during, or after the determination of the trapped volume of the liposomal composition whose quality control is desired. As a further alternative, the standard trapped volume may be an absolute figure based on previous analyses. If the measured trapped volume differs from the standard reference values in a significant manner (more than ±10%) then this difference indicates a production failure.

Additionally or alternatively, the trapped volume can be used to calculate the concentration of API encapsulated within the liposomes. The concentration of API can then be used for controlling the quality of a liposomal composition by comparing it with a reference concentration and rejecting said liposomal composition if the determined API concentration is different from the reference concentration by more than plus or minus 10%. The reference API concentration can be an amount which is known to be acceptable for exerting therapeutic benefit in patients to be treated with said API. The reference API concentration may be a precise figure, or it may be a range. For example, it may be an absolute amount with an acceptable percentage deviation or a standard API concentration range. If the API concentration of a liposomal composition as determined by the methods of the present invention falls outside the range of reference concentrations by more than plus or minus 10%, the liposomal composition is rejected.

As indicated above, the methods of the present invention advantageously provide post-production determination of the trapped volume. Accordingly, only a small portion of the sample can be collected for use in the methods of the present invention while the remaining composition can be used for clinical and other applications. Typically, several samples are collected for determination of the trapped volume in order to minimize the effects of experimental deviation, non-uniform collection and/or non-representative collection of samples. Thus, within the scope of the present invention is a comparison of an average value against the reference values.

Also included within the scope of the present invention is a liposomal composition formulated for intra-articular administration comprising a fluid medium; a polyol tonicity agent; and a plurality of liposomes consisting essentially of 1,2-Dimyristoyl-sn-Glycero-3-Phosphocholine (DMPC), and 1,2-Dipalmitoyl-sn-Glycero-3-Phosphocholine (DPPC) at a ratio of about 45:55 which is essentially free of an active pharmaceutical ingredient. The term "essentially free of an active pharmaceutically ingredient", as used herein, refers in some embodiments to a liposomal composition that includes less than a therapeutically effective amount of the active pharmaceutically ingredient, which is known for use in joint lubrication, treatment of joint dysfunction, reduction of joint pain, irritation and/or wear, or any combination thereof. In some embodiments, the liposomal composition does not include a lubrication agent, such as, inter alia, a glycosaminoglycan or a pharmaceutically acceptable salt, ester or derivative thereof such as hyaluronic acid or hyaluronan-containing salt or ester. The plurality of liposomes in said liposomal composition is characterized by a specific trapped aqueous volume in the range of about 1 to about 4 μl/mg lipid as determined by any of the methods disclosed herein, including each value within the specified range.

According to some aspects and embodiments, the fluid medium comprises a histidine buffer. According to other aspects and embodiments, the polyol is a linear polyol. According to additional aspects and embodiments, the polyol is a sugar or a sugar alcohol having at least five hydroxyl groups. Exemplary polyols include, but are not limited to, mannitol, dextrose, lactose, trehalose and combinations thereof. Each possibility represents a separate embodiment. Currently preferred is the use of mannitol as the polyol. According to various embodiments, the weight ratio between the plurality of liposomes and the polyol ranges from about 6:1 to about 2:1, including all iterations of ratios within the specified range.

Encompassed by the present invention is a liposomal composition having a specific trapped aqueous volume in the range of about 1 to about 4 μl/mg lipid as measured by any of the methods disclosed herein, the liposomal composition comprising a fluid medium, a polyol and a plurality of liposomes consisting essentially of a combination of DMPC and DPPC, wherein DMPC is present in a weight percent ranging from about 1% (w/w) to about 10% (w/w), and DPPC is present in a weight percent ranging from about 2% (w/w) to about 12% (w/w), including each value within the specified ranges. Typically, the liposomal composition has a pH in the range of about 5 to about 8, including each value within the specified range.

In certain aspects and embodiments, the plurality of liposomes in said liposomal composition is characterized by a specific trapped aqueous volume in the range of about 1.5 to about 3.5 μl/mg lipid, or about 2 to about 3 μl/mg lipid, including each value within the specified ranges. In other aspects and embodiments, the plurality of liposomes in said liposomal composition is characterized by a trapped aqueous volume in the range of about 10% to about 35%, or about 20% to about 30%, including each value within the specified ranges.

As used herein and in the appended claims, the singular forms "a", "an", and "the" include plural references unless the context clearly dictates otherwise. Thus, for example, reference to "a lipid" includes a plurality of such lipids. It should be noted that the term "and" or the term "or" is generally employed in its sense including "and/or" unless the context clearly dictates otherwise. As used herein, the term "about" is meant to encompass variations of ±10%.

The following examples are presented in order to more fully illustrate certain embodiments of the invention. They should in no way, however, be construed as limiting the broad scope of the invention. One skilled in the art can readily devise many variations and modifications of the principles disclosed herein without departing from the scope of the invention.

EXAMPLES

Comparative Example: Determination of the Trapped Aqueous Phase of Liposomes Using Potassium Ferricyanide Dye The trapped aqueous volume (Vtaq) of a liposomal composition containing empty liposomes formed from 1,2-Dimyristoyl-sn-Glycero-3-Phosphocholine (DMPC), and 1,2-Dipalmitoyl-sn-Glycero-3-Phosphocholine (DPPC) at a ratio of about 45:55, by hydrating the phospholipids-containing mixture with a solution containing 10 mM histidine buffer pH 6.5 in 4% mannitol was assessed.

Figure 2:
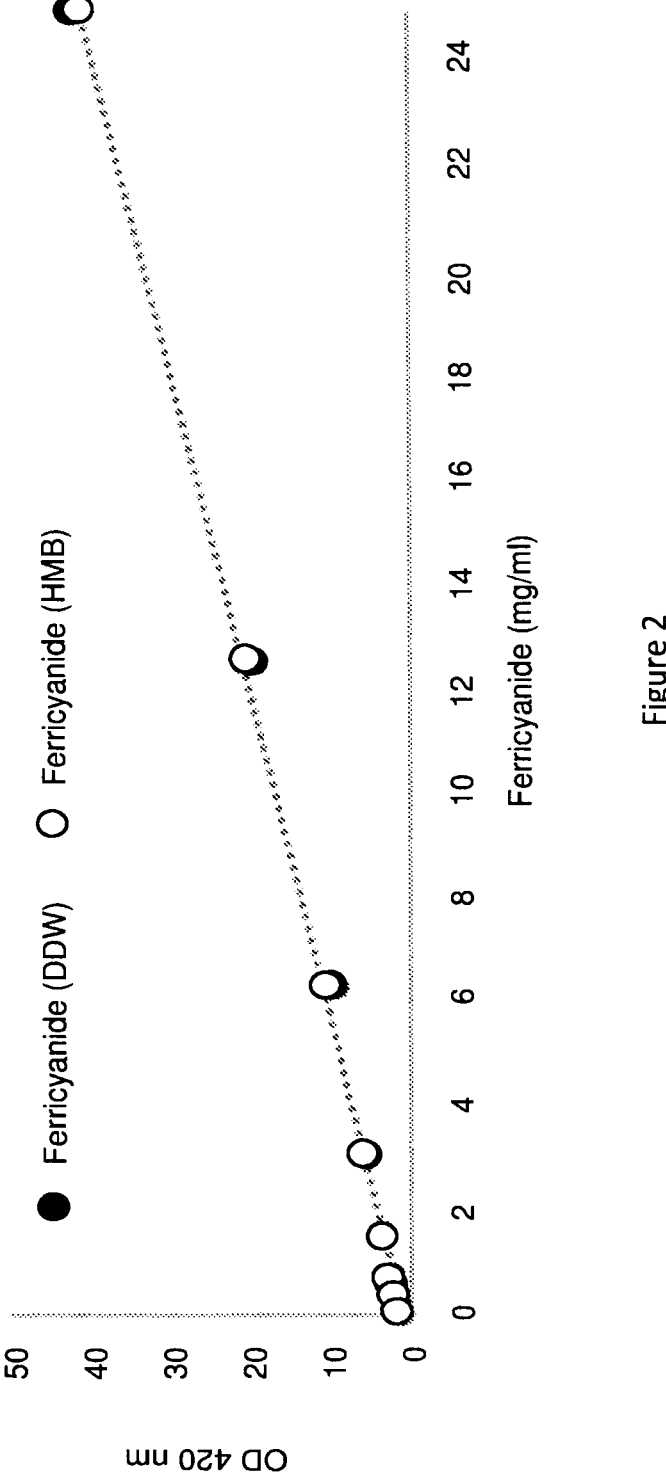
FIG. 2 is a calibration curve of the optical density of ferricyanide at a wavelength of 420 nm in water and HMB.

A common method used to determine the trapped Vt and Vtaq is based on the use of a dye that neither interacts with the liposomal membranes nor permeates the liposomes, such as potassium ferricyanide. The use of potassium ferricyanide for the determination of Vt was performed as described below:

A standard solution of potassium ferricyanide (0.2 mg/mL) was prepared and mixed with a pre-weighed sample of a liposomal composition (containing empty liposomes which are drug free). In order to remove small (sub-micron) liposomes, the sample was centrifuged for 10-30 min at 14,000 rpm. The supernatant was then removed and weighed. The standard solution of potassium ferricyanide was added to the liposome-containing precipitant at a 1:1 weight ratio followed by mixing using Vortex and centrifuging for 30-60 min at 14,000 rpm. It is noteworthy that due to the difficulty in mixing, long vortexing, heating, and sonication were used. The supernatant solution was then collected. Absorbance of the ferricyanide dye was determined using UV-VIS spectrophotometry at 420 nm and the concentration of the ferricyanide was calculated based on a calibration curve performed under the same conditions (FIG. 2).

An alternative procedure was also employed. A standard solution of potassium ferricyanide (1.25-50 mg/mL) was prepared and added to about 1 gram of a pre-weighed sample of a liposomal dispersion of empty (drug free) liposomes followed by mixing using Vortex and centrifuging for 1-3 hrs at 14,000 rpm. The supernatant solution was collected and the absorption of the ferricyanide concentration was determined using UV-VIS spectrophotometry at 420 nm and 600 nm. Since ferricyanide does not absorb light at 600 nm, any absorption at this wavelength is attributed to the contribution of turbidity of small liposomes in the supernatant (Barenholz et al., Liposome Technology 1, 1993, 527-616). As the absorbance of the total liposome dispersion could not be determined due to very high turbidity, in order to calculate the Vt, the absorbance of the supernatant was read at 420 nm against a reference dispersion of the same volume that lacked liposomes. The turbidity of the supernatant of the liposome dispersion interfered with obtaining a consistent absorbance value at 420 nm and therefore no reliable values of Vt and Vtaq could be determined using this method ($OD_{420nm}$ of the supernatant (without ferricyanide) was 0.065 compared to 0.049 of the histidine mannitol buffer alone).

Figure 3:
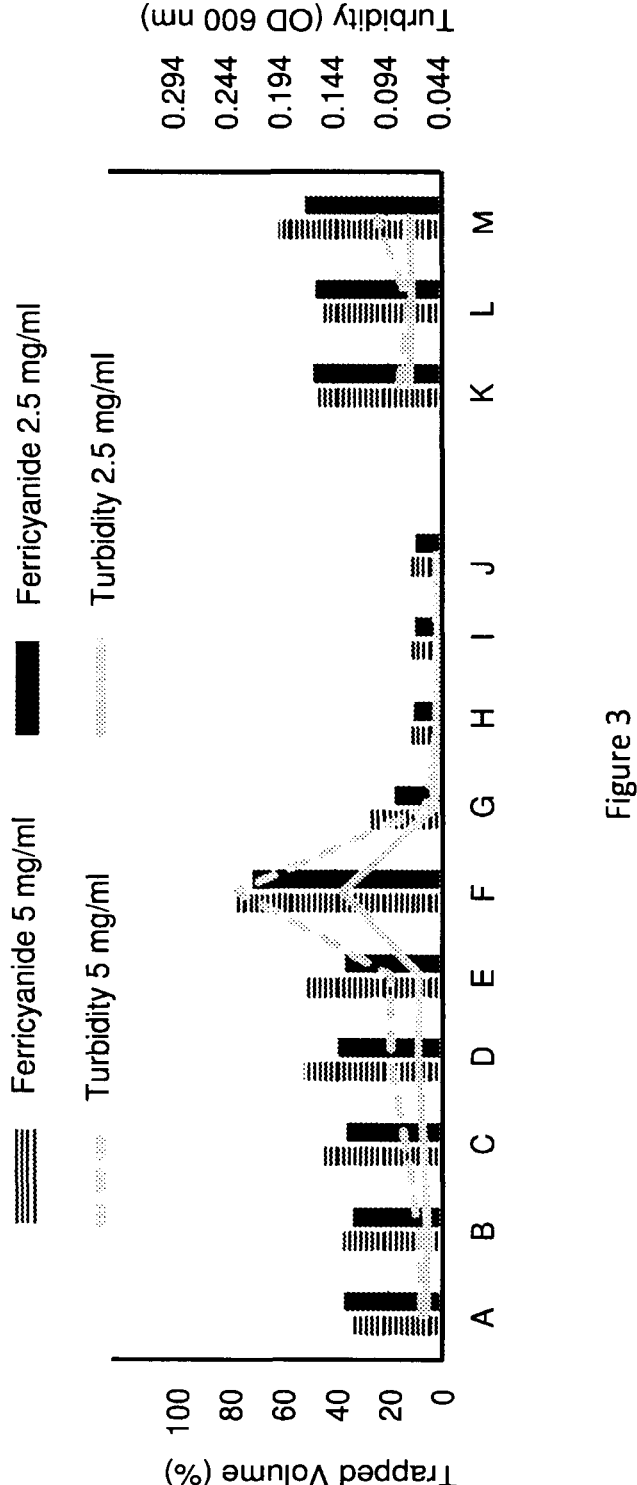
FIG. 3 is a diagram of the trapped volume and turbidity of the upper phase of different samples as determined using a ferricyanide dye. A—3 mM lipid; B—52 mM lipid; C—122 mM lipid; D—160 mM lipid; E—206 mM lipid.

The results (FIG. 3) demonstrate the effect of turbidity in the supernatant on the absorbance at 420 nm. In particular, even after 2 hrs of centrifugation, the turbidity was relatively high, i.e. optical density values of the liposomes in the upper phase at 600 nm of 0.055-0.063. The absorbance at 600 nm indicates that a much larger turbidity at 420 nm exists. Accordingly, the values of Vt obtained by this method are false. Therefore no Vt can be calculated with this approach for an MLV composition containing DMPC/DPPC phospholipids.

Example 1: Determination of the Trapped Volume and Trapped Aqueous Volume of Liposomes Using $^{14}$C-carboxyl-inulin An alternative approach was therefore developed which is not absorbance dependent. $^{14}$C-carboxyl-inulin that does not interact and/or permeate the liposomes was selected as the tracer/marker.

The trapped aqueous volume (Vtaq) of a liposomal composition containing empty liposomes formed from 1,2-Dimyristoyl-sn-Glycero-3-Phosphocholine (DMPC), and 1,2-Dipalmitoyl-sn-Glycero-3-Phosphocholine (DPPC) at a ratio of about 45:55, by hydrating the phospholipids-containing mixture with a solution containing 10 mM histidine buffer pH 6.5 in 4% mannitol was assessed using $^{14}$C-carboxyl-inulin as a radioactive marker. The determination of Vt and Vtaq and specific Vt and Vtaq of the liposomal composition was performed using two approaches based on the supernatant and pellet (FIG. 4).

[14]C-carboxyl-inulin solution (in water) was added to a pre-weighed sample containing the liposomal composition. A portion of the sample (100-200 mg) was transferred into a pre-weighed 20 mL scintillation vial and then weighed. Another portion (250-350 mg) was transferred into an Eppendorf tube and centrifuged at 20817 relative centrifugal force (rcf) for 30 min at 4° C. (Centrifuge 5810 R; Eppendorf, Germany). The aqueous supernatant was collected and transferred into a pre-weighed Eppendorf tube and then weighed again. A portion of the supernatant in the range of ~100-200 mg was transferred into a pre-weighed scintillation vial and then weighed. A solvable was added and the solution was mixed for ~1 hr at 50° C. to solubilize the liposomes. Liquid scintillation cocktail (Opti-Fluor) was added to each vial and the vials were stored overnight protected from light at 5-8° C. The radioactivity count as disintegration per minute (DPM) was determined in a liquid scintillation beta-counter (Packard 1900 TR Scintillation Counter).

The trapped aqueous volume (Vtaq) was calculated by two methods (FIG. 4). In the first method, the total trapped volume (Vt) occupied by the liposomes (Vt, which includes the lipid volume plus the trapped aqueous volume Vtaq) was calculated from the ratio between the DPM/ml of the supernatant and the DPM/ml of the total liposome dispersion (before liposome precipitation). This ratio enables the calculation of the % of total volume occupied by the liposomes from the total amount of the liposomal dispersion. The above ratio can be converted into volume. Vtaq was then calculated by subtracting the lipid volume from Vt. Vtaq was calculated according to equations 1-3 above, where $V_{free}$ is the volume of the supernatant plus the interstitial volume; $V_{interstitial}$ is the free (non-liposomal) aqueous volume between the precipitated liposomes following centrifugation, and $V_{lipids}$ is the volume of lipids calculated from their mass divided by their density. $V_{free}$ (also includes $V_{interstitial}$) was calculated according to equation 1.

The relative standard deviation (% RSD) was calculated for this determination (n=5). The specific trapped aqueous volume (Vtaq) calculated based on the upper phase (supernatant) radioactivity was 1.9±0.06 μl/mg lipid. The specific trapped volume (Vt) calculated based on the upper phase radioactivity was 2.9±0.06 μl/mg lipid with % RSD of 2.9% (FIG. 4).

Example 2: Determination of Trapped Volume at Different Lipid Concentrations The liposomal sample was diluted with 10 mM iso-osmotic histidine buffer pH 6.5 in 4% mannitol. The specific trapped aqueous volume was determined as described in Example 1 based on the ratio of the DPM/ml of the supernatant and the DPM/ml of the total liposome dispersion. A linear correlation was found between the total lipid concentration and the % trapped aqueous volume. The relative standard deviation increased exponentially as the lipid concentration decreased (FIG. 5). The specific Vtaq of the liposomal sample was calculated by normalizing it with the lipid weight to determine the average specific trapped aqueous volume (n=15) (μl trapped volume/mg lipid). The specific Vtaq obtained was 2.0±0.3 μl/mg lipid (FIG. 6). The results clearly demonstrate that the specific Vtaq (μl/mg lipid) remains the same irrespective of the total lipid concentration for the same liposomal composition. Thus, the method for determining the trapped volume is consistent and reliable. The fact that the specific trapped volume is independent of lipid (liposome) concentration clearly supports the lack of interaction between the $^{14}$C-carboxy inulin and the liposomes.

Example 3: Determination of Trapped Volume at Different $^{14}$C-carboxyl-inulin Concentrations In order to verify that the determination of the trapped aqueous volume (Vtaq) is not affected by the interaction of $^{14}$C-carboxyl-inulin with the liposomes, the aqueous trapped volume at different $^{14}$C-carboxyl-inulin concentrations was determined as described in Example 1 based on the radioactivity of the supernatant. FIG. 7 shows that the average specific trapped aqueous volume (n=6) was 2.2%±0.1 with RSD of 4.3% indicating that $^{14}$C-carboxyl-inulin, when added to a pre-formed liposome dispersion, does not interact with the liposome membrane or permeate into the liposomes. This is also confirmed in Schafer et al., American Journal of Physiology-Legacy Content 206, 1964, 985-991.

Example 4: Determination of Trapped Volume of Multilamellar Vesicles (MLVs) vs. Large Multivesicular Vesicles (LMVVs)

In order to substantiate the utility of using the $^{14}$C-inulin approach to determine Vt and Vtaq as a reliable descriptor of the quality of a liposome dispersion, a comparison between Vt and Vtaq of liposomal compositions containing multilamellar vesicles (MLVs) and large multivesicular vesicles (LMVVs) was performed. The LMVVs liposomal composition was prepared from MLVs by repetitive cycles of freezing and thawing as described in Cohen et al., Journal of Controlled Release 160, 2012, 346-352.

A liposomal composition composed of MLVs was prepared as follows. MLVs of hydrogenated soybean phosphatidylcholine (HSPC) and cholesterol at a mole ratio of 2:1 or HSPC alone, were prepared in saline by mixing the phosphatidylcholine (with/out cholesterol) in ethanol at 65-70° C. followed by its injection into an aqueous solution (either water or saline). The liposomal composition contained a phosphatidylcholine concentration of ~75 mM. A portion of the composition was then subjected to ten cycles of freezing and thawing in order to induce the conversion of MLVs to LMVVs. Repeated cycles of freeze-thawing of liposomes is known to cause a dramatic increase in the aqueous trapped volume (Sriwongsitanont et al., The Open Colloid Science Journal, 4, 2010, 1-6; Elorza et al., Journal of microencapsulation, 10(2), 1993, 237-248; Mayer et al., Biochimica et Biophysica Acta (BBA)-Biomembranes, 817(1), 1985, 193-196). During freezing, the bilayer of the liposomes is disrupted and destabilized (MacDonald et al., Liposome Technology, 1, 1993, 209-228), while during thawing, the exposed hydrophobic cores fuse to form new vesicles with decreased number of lamella (Pick, Archives of biochemistry and biophysics, 212(1), 1981, 186-194).

Liposomes were characterized for their size distribution and phosphatidylcholine concentration. Although both MLV- and LMVV-containing samples (of the same lipid composition) had the same lipid concentration and similar mean diameter (though somewhat different size distribution), visual inspection of the vials following centrifugation showed a large increase in pellet volume of LMVVs vs. MLVs. The trapped volume of LMVVs (Vt) and even more so the trapped aqueous volume Vtaq were also found to be significantly larger than those of MLVs.

The results are summarized in Table 1 and shown in FIG. 8.

TABLE 1

| Sample ID | Lipid Concen. (mM) | Mean diameter (μm) | Vtaq (%) | Specific Vtaq (μl trapped aqueous volume/mg Lipid) | Vt (%) | Specific Vt (μl trapped volume/ mg Lipid) | Vtaq/Vt |
|---|---|---|---|---|---|---|---|
| MLV HSPC/CHOL | 108 | 11.4 ± 7.7 | 14.7 ± 2.8 | 2.9 ± 0.6 | 19.8 ± 2.8 | 3.9 ± 0.6 | 0.74 |
| LMVV HSPC/CHOL | 108 | 10.7 ± 5.5 | 42.5 ± 1.8 | 8.3 ± 0.4 | 47.6 ± 1.8 | 9.3 ± 0.4 | 0.89 |
| MLV HSPC | 76 | 9.1 ± 6.8 | 10.1 ± 1.0 | 1.9 ± 0.2 | 15.5 ± 1.0 | 2.9 ± 0.2 | 0.65 |
| LMVV HSPC | 76 | 9.1 ± 5.4 | 56.7 ± 0.7 | 10.5 ± 0.1 | 62.1 ± 0.7 | 11.5 ± 0.1 | 0.91 |

Thus, the method of the present invention provides an accurate measurement of Vt, Vtaq, specific Vt, and specific Vtaq showing a significant difference in the trapped volume of MLVs compared to LMVVs. In particular, the trapped volume of LMVVs was significantly higher than the trapped volume of MLVs.

Example 5: Comparison of Trapped Volume Measured Using the Method of the Present Invention and a Method Utilizing Calcium Ions as a Trapped Marker To further validate the $^{14}$C-inulin-based method to determine Vtaq, a method that directly determines the trapped volume by encapsulating a marker inside the aqueous phase of the liposomes during lipid hydration was applied and compared to the method of the present invention. In particular, calcium ions were selected as a water soluble membrane impermeable marker to directly determine Vtaq on MLVs composed of DMPC/DPPC at a 45:55 mole ratio. The liposomes were prepared by injecting a mixture of the lipids in ethanol into an aqueous medium containing 20 mM calcium ions (as calcium acetate) in 10 mM histidine buffer pH 6.5 in 4% mannitol (histidine mannitol buffer, HMB). Buffer exchange and removal of the ethanol and non-encapsulated calcium ions was performed by repeated cycles of precipitation (by centrifugation) and repeated washings of the liposomes using the same HMB without calcium acetate. These repeated cycles of precipitation and washings of the MLVs were performed in order to ensure substantially complete removal of the external medium containing the calcium and replacing it with iso-osmotic HMB. The pH and osmolality of the washing medium and the hydration medium containing calcium acetate were adjusted to 6.5, 272 and 279 mOsmo/kg, respectively. The external medium containing the calcium ions was replaced with HMB medium by 5 consecutive cycles of centrifugation and washing steps. The lipid concentration and osmolality of the final liposomal dispersion were 148 mM total PCs (105 mg/mL) and 279 mOsmo/kg, respectively. The concentration of the trapped calcium ions inside the liposomes was determined using Inductively Coupled Plasma (IPC)-Optical Emission Spectrometry (ICP-OES). In order to correct for the interstitial volume and subtract its contribution from the intra-liposomal calcium amount, the interstitial volume using the $^{14}$C-inulin added to the liposome dispersion post liposome preparation (as described above, by measuring the radioactivity of the precipitate comprising a plurality of liposomes and interstitial medium between the liposomes) was determined. For comparison, the aqueous trapped volume of the same liposomal composition was also determined using the $^{14}$C-inulin external marker as described in Example 1 from the ratio between $(DPM/ml)_{sup}$ and $(DPM/ml)_{total}$.

The concentration of calcium was determined using ICP-OES before and after buffer exchange and removal of ethanol and calcium ions from the extra liposomal medium by repeated cycles of centrifugation and washings. The concentration of residual calcium in the external medium after centrifugation was also determined in the liposomes' upper phase. Due to the high organic load, liposomal samples were treated by acid digestion at 200° C. for 4 hrs which is not expected to affect the calcium determination. The total lipid concentration was determined using the modified Bartlett procedure (Shmeeda H., et al., Methods in enzymology, 367, 2003, 272).

The trapped aqueous volume (Vtaq) was calculated according to the following equation:

$$\frac{\left(\frac{[Calcium_2] - [Calcium_e]}{[Lipid_2]}\right)}{\left(\frac{[Calcium_1]}{[Lipid_1]}\right)} - V_{interstitial} - V_{lipid} = V_{trapped\ aqueous}$$

where $Calcium_1$ and $Calcium_2$ are the total concentration of calcium before and after buffer exchange, respectively; $Lipid_1$ and $Lipid_2$ are the total lipid concentration before and after buffer exchange, respectively; $Calcium_e$ is the concentration of residual calcium in the external volume after buffer exchange; $V_{interstitial}$ is the volume of interstitial fluid determined by $^{14}$C-inulin in the pellet; and $V_{lipids}$ is calculated from known lipid concentration, assuming density~1. The results of calcium concentrations and lipid concentrations of the different samples are summarized in Table 2.

TABLE 2

|  | Calcium (mM) | Lipid (mM) |
| --- | --- | --- |
| Total before buffer exchange | 19.27 | 202 |
| Total after buffer exchange | 6.034 | 148 |
| Upper phase after buffer exchange | 0.109 | not relevant |

The trapped aqueous volume (Vtaq) as determined by the trapped calcium marker was 24.42% (% $Vt_{aq}$=((6.034−0.109)/148×202/19.27)×100%−7.1%−10.45%=24.42%) with specific trapped aqueous volume (Vtaq) of 2.3 µl/mg lipid and specific trapped volume (Vt) of 4 µl/mg lipid. The external volume was also calculated using the external calcium concentration before buffer exchange which was determined as 58%. Both results were compared to the method of the present invention using $^{14}$C-inulin marker as follows: The aqueous trapped volume of the liposomes was determined using two different approaches: 1—based on the ratio of the radioactivity of the supernatant compared to total radioactivity, and 2—based on the radioactivity of the pellet (which is the radioactivity of the interstitial fluid). Similar results were obtained using both approaches. The relative standard deviation (% RSD) was calculated for both approaches (n=5). The results of the calculated specific trapped aqueous volume (Vtaq) and the specific trapped volume (Vt) are summarized in Table 3.

TABLE 3

|  | | | Specific Vtaq | | |
| --- | --- | --- | --- | --- | --- |
|  | Vtaq | | µl/mg | | % RSD |
|  | (%) | STDEV | lipid | STDEV | (n = 5) |
| $^{14}$C-Inulin method (Upper phase) | 24.1 | 0.87 | 2.3 | 0.08 | 3.6 |
| $^{14}$C-Inulin method (Pellet) | 24.9 | 0.48 | 2.4 | 0.05 | 1.95 |

Thus, the results of the trapped aqueous volume (Vtaq) of the liposomes obtained by trapped calcium ions (inside the liposomes) as a marker are almost identical to the results obtained by the radioactive $^{14}$C-inulin external marker. Accordingly, the use of $^{14}$C-inulin external liposome-medium marker to determine Vt and Vtaq of a liposome dispersion according to certain embodiments of the present invention provides an easy, simple, sensitive, reliable, accurate, and reproducible method. The method can be applied to pre-formed liposomal dispersions and does not require inclusion of the marker inside the liposomes. The method was also shown to be independent on the turbidity of the supernatant following liposome precipitation and therefore overcomes the problems that are often encountered when using low molecular weight chromophore as the marker to determine the extra-liposome medium. As this method enables the determination of both Vt and Vtaq, it is an important descriptor of liposome properties and can be used for quality assurance of pre-formed liposomes.

While certain embodiments of the invention have been illustrated and described, it is to be clear that the invention is not limited to the embodiments described herein. Numerous modifications, changes, variations, substitutions and equivalents will be apparent to those skilled in the art without departing from the spirit and scope of the present invention as described by the claims, which follow.

What is claimed is:

1. A method of determining the trapped volume (Vt) and the trapped aqueous volume (Vtaq) of a plurality of liposomes in a liposomal composition, the method comprising the steps of:
   (i) obtaining a liposomal composition comprising a plurality of liposomes at a predetermined concentration of lipids which are suspended or dispersed in a fluid medium;
   (ii) adding a marker to said liposomal composition, wherein the marker is liposome impermeable and has a molecular weight equal to or higher than 1 kDa;
   (iii) measuring a signal induced by the marker in said liposomal composition thereby determining the total volume of the liposomal composition;
   (iv) separating the fluid medium from the plurality of liposomes thereby obtaining a fluid medium and a precipitate comprising a plurality of liposomes and an interstitial medium between the liposomes;
   (v) measuring a signal induced by the marker in the separated fluid medium of step (iv) thereby determining the volume of the fluid medium and the interstitial medium;
   (vi) optionally measuring a signal induced by the marker in the precipitate comprising a plurality of liposomes and an interstitial medium between the liposomes of step (iv) thereby determining the interstitial volume between the liposomes in the precipitate; and
   (vii) calculating the trapped volume (Vt) and the trapped aqueous volume (Vtaq) of the plurality of liposomes based on the volumes determined in steps (iii) and (v) or in steps (iii), (v), and (vi) and the predetermined concentration of step (i).

2. The method of claim 1, wherein determining the trapped volume (Vt) of a plurality of liposomes in a liposomal composition comprises determining the specific trapped volume or the specific trapped aqueous volume.

3. The method of claim 1, wherein step (vi) is performed and step (vii) comprises calculating the trapped volume (Vt) and the trapped aqueous volume (Vtaq) of the plurality of liposomes based on the volumes determined in steps (iii), (v), (vi), and the predetermined concentration of step (i).

4. The method of claim 1, wherein step (vi) is not performed and step (vii) comprises calculating the trapped volume (Vt) and the trapped aqueous volume (Vtaq) of the plurality of liposomes based on the volumes determined in steps (iii), (v), and the predetermined concentration of step (i).

5. The method of claim 4, wherein step (vii) comprises calculating the ratio between the signal induced by the marker in the fluid medium following step (iv) and the signal induced by the marker in the liposomal composition prior to step (iv).

6. The method of claim 1, wherein the marker is water soluble; and/or wherein the marker has a molecular weight of at least about 2 kDa; and/or wherein the marker is a radioactive marker, or wherein the marker is $^{14}C$-carboxy inulin.

7. The method of claim 1, wherein the liposomal composition comprises a plurality of liposomes selected from the group consisting of unilamellar vesicles (SUV), large unilamellar vesicles (LUV), giant unilamellar vesicles (GUV), oligolamellar vesicles (OLV), multilamellar vesicles (MLV), multivesicular liposomes (MVL), and a mixture or combination thereof; and/or wherein the liposomal composition comprises a plurality of liposomes in sizes ranging from about 0.3 μm to about 50 μm; and/or wherein the liposomal composition comprises a plurality of liposomes at a lipid concentration of about 50 mM to about 300 mM; and/or wherein the liposomal composition comprises a plurality of empty liposomes essentially free of an active pharmaceutical agent.

8. The method of claim 1, wherein the liposomal composition comprises a plurality of liposomes encapsulating an active pharmaceutical ingredient, and wherein the method further comprises determining the concentration of the active pharmaceutical ingredient encapsulated by the plurality of liposomes.

9. The method of claim 1, wherein step (iv) provides a fluid medium which is substantially devoid of liposomes; and/or wherein step (iv) is performed by centrifugation, filtration, or decantation.

10. The method of claim 9, wherein step (iv) is performed by centrifugation.

11. The method of claim 10, wherein step (iv) is performed at a relative centrifugal force of about 10,000 to about 30,000 (×g) and/or wherein step (iv) is performed at a temperature of about 2° C. to about 25° C.; and/or wherein step (iv) is performed for a time period in the range of about 10 minutes to about 100 minutes.

12. A method for controlling the quality of a liposomal composition, the method comprising:
   (i) determining the trapped volume (Vt) and the trapped aqueous volume (Vtaq) of a plurality of liposomes in a liposomal composition according to claim 1;
   (ii) comparing the determined trapped volume (Vt) and trapped aqueous volume (Vtaq) with reference trapped volume (Vt) and trapped aqueous volume (Vtaq) values; and
   (iii) rejecting said liposomal composition if the determined trapped volume (Vt) and trapped aqueous volume (Vtaq) differ from the reference values by more than plus or minus 10%.

13. The method of claim 12, wherein the liposomal composition comprises an active pharmaceutical ingredient encapsulated within a plurality of liposomes, and wherein the method comprises:
   (i) determining the concentration of the active pharmaceutical ingredient encapsulated within a plurality of liposomes;

(ii) comparing the determined active pharmaceutical ingredient concentration with a reference active pharmaceutical ingredient concentration; and (iii) rejecting said liposomal composition if the determined active pharmaceutical ingredient concentration differs from the reference active pharmaceutical ingredient concentration by more than plus or minus 10%.

14. A liposomal composition formulated for intra-articular administration comprising a fluid medium; a polyol tonicity agent; and a plurality of liposomes consisting essentially of 1,2-Dimyristoyl-sn-Glycero-3-Phosphocholine (DMPC), and 1,2-Dipalmitoyl-sn-Glycero-3-Phosphocholine (DPPC) at a ratio of about 45:55, wherein the composition is essentially free of an active pharmaceutical agent, and wherein the plurality of liposomes are characterized by a specific trapped aqueous volume in the range of about 1 to about 4 µl/mg lipid as determined by a method comprising the steps of:

(i) adding a marker to said liposomal composition, wherein the marker is liposome impermeable and has a molecular weight equal to or higher than 1 kDa;

(ii) measuring a signal induced by the marker in said liposomal composition thereby determining the total volume of the liposomal composition;

(iii) determining the volume of the fluid medium and the interstitial medium between liposomes obtained by separating the fluid medium from the plurality of liposomes and measuring a signal induced by the marker in the fluid medium following separation; and (iv) calculating the trapped volume (Vt) and trapped aqueous volume (Vtaq) of the plurality of liposomes based on the volumes determined in steps (ii) and (iii) and the concentration of the lipids forming the liposomes.

15. The liposomal composition of claim 14, wherein step (iii) further comprises determining the interstitial volume between liposomes in a precipitate by measuring a signal induced by the marker in the precipitate following separation.

16. The liposomal composition of claim 14, wherein the marker has a molecular weight of at least about 2 kDa; and/or wherein the marker is water soluble; and/or wherein the marker is a radioactive marker or wherein the marker is $^{14}$C-carboxy inulin.

17. The liposomal composition of claim 14, wherein separating the fluid medium from the plurality of liposomes is performed by centrifugation.

18. The liposomal composition of claim 14, wherein the plurality of liposomes are selected from the group consisting of unilamellar vesicles (SUV), large unilamellar vesicles (LUV), giant unilamellar vesicles (GUV), oligolamellar vesicles (OLV), multilamellar vesicles (MLV), multivesicular liposomes (MVL), and a mixture or combination thereof; and/or wherein the plurality of liposomes have sizes ranging from about 0.3 µm to about 50 µm; and/or wherein the concentration of the lipids forming the liposomes is in the range of about 50 mM to about 300 mM; and/or wherein the concentration of the lipids forming the liposomes is in the range of about 100 mM to about 200 mM; and/or wherein the composition has a pH of about 5 to about 8.

19. The liposomal composition of claim 14, wherein the fluid medium is a histidine buffer; and/or wherein the polyol is a linear polyol; and/or wherein the polyol is selected from the group consisting of mannitol, dextrose, lactose, trehalose and combinations thereof; and/or wherein the polyol is mannitol; and/or wherein DMPC is present in the composition in a weight percent ranging from about 1% (w/w) to about 10% (w/w), and DPPC is present in the composition in a weight percent ranging from about 2% (w/w) to about 12% (w/w).

20. The liposomal composition of claim 14, wherein the specific trapped aqueous volume is in the range of about 1.5 to about 3.5 µl/mg lipid; and/or wherein the trapped aqueous volume is in the range of about 10% to about 35%.

* * * * *